(12) United States Patent
Anderson

(10) Patent No.: US 10,299,784 B2
(45) Date of Patent: May 28, 2019

(54) SUTURE BUTTON CONSTRUCT FOR SURGICAL PROCEDURES

(71) Applicant: Christian N. Anderson, Nashville, TN (US)

(72) Inventor: Christian N. Anderson, Nashville, TN (US)

( * ) Notice: Subject to any disclaimer, the term of this patent is extended or adjusted under 35 U.S.C. 154(b) by 0 days.

(21) Appl. No.: 15/643,173

(22) Filed: Jul. 6, 2017

(65) Prior Publication Data

US 2019/0008502 A1   Jan. 10, 2019

(51) Int. Cl.
*A61B 17/04* (2006.01)

(52) U.S. Cl.
CPC .. *A61B 17/0401* (2013.01); *A61B 2017/0404* (2013.01); *A61B 2017/0414* (2013.01); *A61B 2017/0417* (2013.01); *A61B 2017/0459* (2013.01); *A61B 2017/0464* (2013.01)

(58) Field of Classification Search
CPC ............ A61B 17/0401; A61B 17/0487; A61B 2017/0404; A61B 2017/0464; A61B 2017/0406; A61B 2017/0414; A61B 2017/0459; Y10T 24/155; Y10T 24/3916; Y10T 24/44983; Y10T 24/15; Y10T 24/36; Y10T 24/3918; Y10T 24/3924; Y10T 24/44923; A61F 2/0811; B65D 33/1625
USPC ........... 606/232, 233, 151; 24/30.5 S, 129 R, 24/570, 129 B, 30.5 R
See application file for complete search history.

(56) References Cited

U.S. PATENT DOCUMENTS

| | | | | |
|---|---|---|---|---|
| 1,306,369 A | * | 6/1919 | Bell | .......................... A44B 1/28 24/129 B |
| 3,409,014 A | * | 11/1968 | Shannon | ................. A61B 10/04 24/129 B |
| 4,291,698 A | | 9/1981 | Fuchs et al. | |

(Continued)

FOREIGN PATENT DOCUMENTS

| EP | 2455002 A1 | 5/2012 |
|---|---|---|
| EP | 2462876 A2 | 6/2012 |

(Continued)

OTHER PUBLICATIONS

Arthrex; www.arthrex.com; Arthroscopic Stabilization of Acute Acromioclavicular Joint Dislocation Using The TightRope System; Surgical Technique; 2010; six pages.

(Continued)

*Primary Examiner* — Katherine M Shi
(74) *Attorney, Agent, or Firm* — Waller Lansden Dortch & Davis, LLP; Matthew C. Cox

(57) ABSTRACT

A suture button for a surgical procedure provides an anchor for pulling and maintaining suture tension through a transosseous tunnel during an operation such as meniscal root repair in the knee. The suture button includes a body having a first tapered longitudinal end, a second tapered longitudinal end, a first side, a second side, an anterior surface and a posterior surface. A first concave notch is defined in the first side, and a second concave notch is defined in the second side. The first notch is open to a first suture dock in the first side, and the second notch is open to a second suture dock in the second side. Each of the first and second suture docks includes a seat to centrally position suture material. A center passage is defined through the suture body at a location between the first and second suture docks.

12 Claims, 12 Drawing Sheets

(56) References Cited

U.S. PATENT DOCUMENTS

| | | | |
|---|---|---|---|
| 4,823,794 A * | 4/1989 | Pierce | A61B 17/0401 606/232 |
| 4,896,366 A * | 1/1990 | Oxman | B65D 33/1625 24/30.5 S |
| D359,229 S * | 6/1995 | Jules | D8/395 |
| 5,645,588 A | 7/1997 | Graf et al. | |
| 6,066,160 A * | 5/2000 | Colvin | A61B 17/0487 606/151 |
| 6,660,023 B2 | 12/2003 | McDevitt et al. | |
| 6,716,234 B2 | 4/2004 | Grafton et al. | |
| 7,217,279 B2 | 5/2007 | Reese | |
| 7,235,091 B2 | 6/2007 | Thornes | |
| 7,390,332 B2 | 6/2008 | Selvitelli | |
| D576,867 S * | 9/2008 | Kretz | D8/356 |
| 7,530,999 B2 | 5/2009 | Clark et al. | |
| 7,594,922 B1 | 9/2009 | Goble et al. | |
| 7,601,165 B2 | 10/2009 | Stone | |
| 7,717,929 B2 | 5/2010 | Fallman | |
| 7,862,584 B2 | 1/2011 | Lyons et al. | |
| 7,905,903 B2 | 3/2011 | Stone | |
| 8,109,968 B2 | 2/2012 | Ashley et al. | |
| 8,128,658 B2 | 3/2012 | Kaiser et al. | |
| 8,162,997 B2 | 4/2012 | Struhl | |
| 8,231,674 B2 | 7/2012 | Albertorio et al. | |
| 8,348,960 B2 | 1/2013 | Michel et al. | |
| 8,439,976 B2 | 5/2013 | Albertorio et al. | |
| 8,460,379 B2 | 6/2013 | Albertorio et al. | |
| 8,545,535 B2 | 10/2013 | Hirotsuka et al. | |
| 8,562,645 B2 | 10/2013 | Stone et al. | |
| 8,591,578 B2 | 11/2013 | Albertorio et al. | |
| 8,663,324 B2 | 3/2014 | Schmieding et al. | |
| 8,753,375 B2 | 6/2014 | Albertorio | |
| 8,821,541 B2 | 9/2014 | Dreyfuss et al. | |
| 8,936,621 B2 | 1/2015 | Denham et al. | |
| 9,017,381 B2 | 4/2015 | Kaiser et al. | |
| 9,107,653 B2 | 8/2015 | Sullivan | |
| 9,173,645 B2 | 11/2015 | Overes | |
| 9,179,907 B2 | 11/2015 | ElAttrache et al. | |
| 9,301,745 B2 | 4/2016 | Dreyfuss | |
| 9,345,471 B2 | 5/2016 | Sullivan | |
| 9,381,013 B2 | 7/2016 | Norton | |
| 9,421,007 B2 | 8/2016 | Brady et al. | |
| 9,451,953 B2 | 9/2016 | Sengun | |
| 9,463,013 B2 | 10/2016 | Pilgeram et al. | |
| 9,468,433 B2 | 10/2016 | Denham et al. | |
| 9,481,493 B2 | 11/2016 | Vantrease | |
| 9,498,202 B2 | 11/2016 | Jafari et al. | |
| 9,510,819 B2 | 12/2016 | Stone et al. | |
| 9,615,821 B2 | 4/2017 | Sullivan | |
| 9,642,610 B2 | 5/2017 | Albertorio | |
| 9,706,985 B2 | 7/2017 | Allen | |
| 2003/0236555 A1 | 12/2003 | Thornes | |
| 2005/0187577 A1 | 8/2005 | Selvitelli et al. | |
| 2005/0197662 A1 | 9/2005 | Clark et al. | |
| 2007/0083236 A1 | 4/2007 | Sikora et al. | |
| 2007/0239209 A1 | 10/2007 | Fallman | |
| 2008/0255613 A1 | 10/2008 | Kaiser et al. | |
| 2009/0105754 A1 | 4/2009 | Sethi | |
| 2010/0256677 A1 | 10/2010 | Albertorio et al. | |
| 2010/0268273 A1 | 10/2010 | Albertorio et al. | |
| 2012/0053630 A1 | 3/2012 | Denham et al. | |
| 2012/0150203 A1* | 6/2012 | Brady | A61B 17/0401 606/148 |
| 2013/0023928 A1 | 1/2013 | Dreyfuss | |
| 2013/0165972 A1 | 6/2013 | Sullivan | |
| 2013/0168478 A1* | 7/2013 | Holman | B65H 75/06 242/118 |
| 2013/0190819 A1 | 7/2013 | Norton | |
| 2013/0345749 A1 | 12/2013 | Sullivan et al. | |
| 2013/0345750 A1 | 12/2013 | Sullivan | |
| 2014/0031864 A1* | 1/2014 | Jafari | A61B 17/0401 606/232 |
| 2014/0114352 A1 | 4/2014 | Allen | |
| 2014/0250636 A1* | 9/2014 | Vantrease | B65D 33/1625 24/30.5 S |
| 2014/0277121 A1 | 9/2014 | Pilgeram et al. | |
| 2016/0030035 A1 | 2/2016 | Zajac et al. | |

FOREIGN PATENT DOCUMENTS

| | | |
|---|---|---|
| EP | 2572648 A1 | 3/2013 |
| EP | 2581047 A1 | 4/2013 |
| EP | 2724673 A1 | 4/2014 |
| EP | 2777513 A1 | 9/2014 |
| EP | 2263608 B1 | 9/2016 |
| JP | H06114067 | 4/1994 |
| KR | 1020130092425 | 8/2013 |
| WO | 2016149283 | 9/2016 |

OTHER PUBLICATIONS

Rosenberg, Thomas D. MD; Smith & Nephew, Inc., Endoscopy Division, ACL Reconstruction with the ACUFEX Director Drill Guide and EnboButton CL Fixation System; Knee Series, Technique Guide, ; 12 pages.

Stryker; www.stryker.com; Joint Preservation; VersiTomic G-Lok, 2011; four pages.

DePuy Synthes Mitek Sports Medicine, Companies of Johnson &Johnson; RIGIDLOOP Adjustable Cortical System Quick Surgical Technique Guide for Soft Tissue ACL Reconstruction; 2014, two pages.

Smith&Newphew; ULTRABUTTON Adjustable Fixation Device; 2016; PN: 71577 Rev. A 02/16; 29 pages.

PCT/US18/41116—International Search Report and Written Opinion, dated Oct. 17, 2018; 12 pages.

Synthes GMBH, English Abstract of KR10-2013-0092425, translation submission date Nov. 26, 2012; 2 pages.

PCT/US18/41059—International Search Report and Written Opinion, dated Jan. 4, 2019; 9 pages.

Takiron, English Abstract of JPH06114067, 1 page.

* cited by examiner

US 10,299,784 B2

SUTURE BUTTON CONSTRUCT FOR SURGICAL PROCEDURES

BACKGROUND

The present invention relates generally to devices and methods for performing arthroscopic surgery on joints and more particularly to suture button devices and associated methods for anchoring and tensioning of sutures during and after surgery.

Various types of sutures, suture fixation devices and associated methods are known in the art for securing a suture in a desired position and/or at a desired tension during and after surgical procedures. In many surgical procedures, a transosseous hole is drilled through a portion of bone, forming a rigid tunnel for passing a surgical instrument or a suture. The drilled tunnel includes a proximal opening adjacent a tissue repair site where a procedure for the repair of tissue is generally performed, such as but not limited to a procedure to repair a meniscus root tear in a knee. The drilled tunnel generally also includes a distal opening at a location remote from the repair site.

During such procedures, one or more sutures are attached to the tissue to be repaired. A free end of the suture is then inserted through the proximal opening of the drilled tunnel and passed away from the repair site to the distal tunnel opening. The suture then exits the distal end of the tunnel and is tensioned to manipulate the damaged tissue into a desired position. The free end of the suture extending out of the distal tunnel opening must be pulled tight to maintain tension on the tissue following the operation. After tension is applied, the suture is fixed in place using an anchor to maintain the desired tension.

Numerous types of suture buttons and suture anchors are known in the art for tying off sutures on the distal end of transosseous tunnels for maintaining tension. However, such conventional suture buttons are often inadequate and may lead to unintentional release of the applied tension on the suture over time. This may cause the tissue to heal improperly, leading to discomfort and pain at the joint and potentially requiring additional operations to reapply the necessary tension.

For example, some conventional suture buttons tend to position the suture at the location passing into the distal tunnel opening in a manner that is axially misaligned with the tunnel opening. This may cause the suture to or rub or chafe against the edge or wall of the drilled tunnel opening, thereby wearing on the suture and eventually loosening or breaking the suture tension over time. Additionally, some conventional suture buttons may cause tension loss because they position the suture material in between the button and the bone tissue at the drilled tunnel opening, causing the bone to impinge on the suture material or to inadvertently torque the suture button leading to loss of tension.

What is needed, then, are improvements in suture button devices and methods for surgical procedures.

BRIEF SUMMARY

The present disclosure generally provides a device and associated methods for anchoring a suture using a suture button during a surgical procedure. The device includes a suture button in some embodiments having an elongated shape with first and second tapered longitudinal ends, and first and second lateral sides. The suture button also includes an anterior surface and a posterior surface. A first side notch is defined in the first lateral side, and a second side notch is defined in the second lateral side. The first side notch opens into a first suture dock defined in the first side, and the second side notch opens into a second suture dock defined in the second side. A center passage is defined through the suture button from the anterior surface to the posterior surface between the first and second suture docks. During use, a portion of a suture is retained in each of the first and second side docks, and the suture passes through the center passage into a drilled transosseous tunnel.

Another object of the present disclosure is to provide a suture button for use with knotless, self-cinching suture constructs for transosseous suture tensioning during medial or lateral meniscal root repair surgical procedures.

A further object of the present disclosure is to provide a suture button for use with conventional knotted suture constructs for transosseous suture tensioning during medial or lateral meniscal root repair surgical procedures.

Yet another object of the present disclosure is to provide a suture button for use with suture constructs having an end with a fixed loop.

Another object of the present disclosure is to provide a suture button configured to secure a fixed loop suture end around the suture button using a lateral girth hitch wherein a portion of the hitched suture extends through a center passage in the suture button into a drilled transosseous tunnel.

Another object of the present disclosure is to provide suture button having first and second tapered ends each shaped for accepting a looped suture construct such that a separate suture may be installed on each tapered longitudinal end of the suture button.

A further object of the present disclosure is to provide a suture button having opposing tapered notches on each side of the suture button, each tapered notch opening to a respective suture dock. Each notch is shaped with a notch gap dimensioned to prevent each suture from backing out of its respective suture dock.

Yet another object of the present disclosure is to provide a suture button having a center passage shaped to accommodate insertion of a fixed loop suture end through the center passage for forming a lateral girth hitch around the suture button.

Another object of the present disclosure is to provide a suture button dimensioned to provide axial alignment between a suture hitched around the suture button and the axial bore of a transosseous drill tunnel.

A further object of the present disclosure is to provide a suture button dimensioned and shaped to prevent impingement of suture material by the edge or wall of a transosseous drill tunnel when the suture button is installed in contact with a patient's bone tissue.

Numerous other objects, features and advantages of the present disclosure will be readily apparent to those skilled in the art upon a reading of the following disclosure when taken in conjunction with the accompanying drawings.

DETAILED DESCRIPTION

Figure 1:
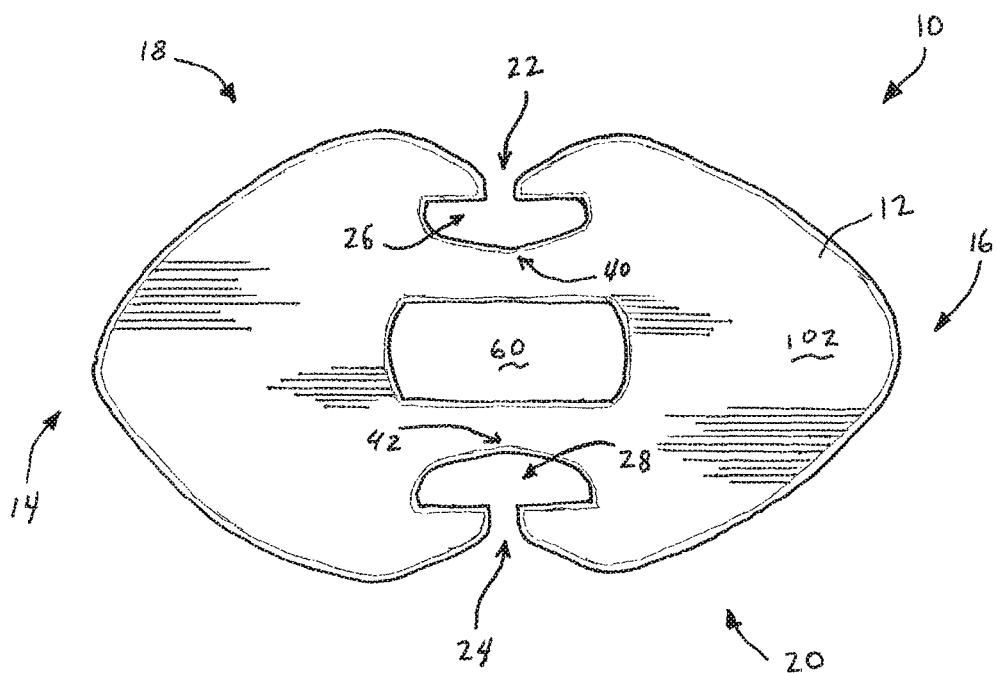
FIG. 1 illustrates a top view of an embodiment of a suture button in accordance with the present disclosure.

Referring now to the drawings, various views of embodiments of a suture button construct and associated suture are illustrated. In the drawings, not all reference numbers are included in each drawing, for the sake of clarity. In addition, positional terms such as "upper," "lower," "side," "top," "bottom," "vertical," "horizontal" etc. refer to the apparatus when in the orientation shown in the drawings or similar orientations. A person of skill in the art will recognize that the apparatus can assume different orientations when in use.

The present disclosure provides a suture button construct for use in surgical procedures. As shown in FIG. 1, suture button 10 is configured to be utilized in surgical procedures requiring a surgeon to pull one or more sutures tight, and to maintain a postoperative tension on the suture within a desired tensile range. Suture button 10 may be specifically configured in some embodiments to maintain suture tension following a repair of a root tear in a medial or lateral meniscus of a human knee using a drilled transosseous tunnel. Alternatively, suture button 10 may be used in numerous other procedures in other parts of the body. Suture button 10 may also be utilized with various techniques and suture constructs, including procedures using one or more knots adjacent the suture button 10 to terminate the suture. Suture button 10 is configured for use with a knotless, self-cinching suture construct in some embodiments.

Suture button 10 provides a construct for securing and positioning a torn or damaged meniscal root during a meniscal root repair operation at a position near its natural anatomical position by maintaining tension on a suture affixed to the root tissue. The tension is applied through a drilled transosseous tunnel. In such procedures, the suture button 10 of the present disclosure allows use of conventional suture constructs and techniques as well as novel knotless, self-cinching suture constructs for meniscal root repair. Thus, the suture button 10 of the present disclosure provides a universal suture button for meniscal root repair and other procedures that is readily interchangeable with a wide range of both conventional and novel suture constructs.

Referring to the drawings a suture button 10 of the present disclosure is shown for example in FIG. 1. Suture button 10 includes an elongated body 12 having a longitudinal length greater than its lateral width. The elongated body 12 of suture button 10 includes a major longitudinal axis and a minor lateral axis. A first longitudinal end 14 is positioned at a first end of the major longitudinal axis, and a second longitudinal end 16 is positioned at the second end of the major longitudinal axis opposite the first longitudinal end 14. First and second ends 14, 16 are each generally formed in a tapered shape sloping to a point at each respective longitudinal end. A first side 18, or first lateral edge, is positioned along a first side of body 12, and a second side 20, or second lateral edge, is positioned along a second side of body 12 opposite first side 18.

Suture button 10 includes a body 12 made of any suitable material for medical device, such as but not limited to a metal material such as titanium or a titanium alloy. In additional embodiments, suture button 10 includes a body 12 constructed of a non-metal material such as but not limited to a polyether ether ketone (PEEK) material, or another polyester plastic material such as polylactic acid (PLLA), blends thereof, or any other suitable material for constructing a suture button for a surgical procedure.

Suture button 10 includes numerous features for securing one or more sutures to the suture button for anchoring a suture. Referring further to FIG. 1, suture button 10 includes a first side notch 22 defined in first side 18. First side notch 22 provides a generally concave indentation along first side 12 between first end 14 and second end 16. First side notch 22 includes a tapered recession providing a location for a suture to be received along the edge of first side 18.

Suture button 10 also includes a second side notch 24 defined in second side 20, generally opposite first side notch 22. Second side notch 24 provides a generally concave indentation along second side 20 of body 12 between first end 14 and second end 16. Second side notch 24 includes a tapered recession providing a location for a suture to be received along the edge of second side 20.

First side notch 22 is open at its innermost point to an interior first suture dock 26 defined in body 12 of suture button 10. First suture dock 26 includes a length in the longitudinal direction greater than its lateral width and greater than the notch gap in first side notch 22, providing a space for one or more sutures to be received. First suture dock 26 includes a first suture dock interior wall having a concave "U" or "V" shape with a central indentation forming first suture dock seat 40, shown in FIG. 1. The sloping profile of the interior wall of first suture dock 26 allows a suture residing in first suture dock 26 to be centrally seated at the first suture dock seat 40 when tensioned. Such placement allows the suture extending from suture button 10 into a transosseous drill tunnel to be axially aligned with the opening of the drill tunnel and to prevent the suture from impinging on the wall or edge of the drill tunnel opening. This placement provides an advantage over some conventional suture buttons that position the suture around the periphery of the suture button away from the centerline of the suture button, which may cause the suture to become angled at its entry to the drill tunnel opening, resulting in undesirable contact between the suture and the drill tunnel opening edge or wall and loss of tension.

Figure 10:
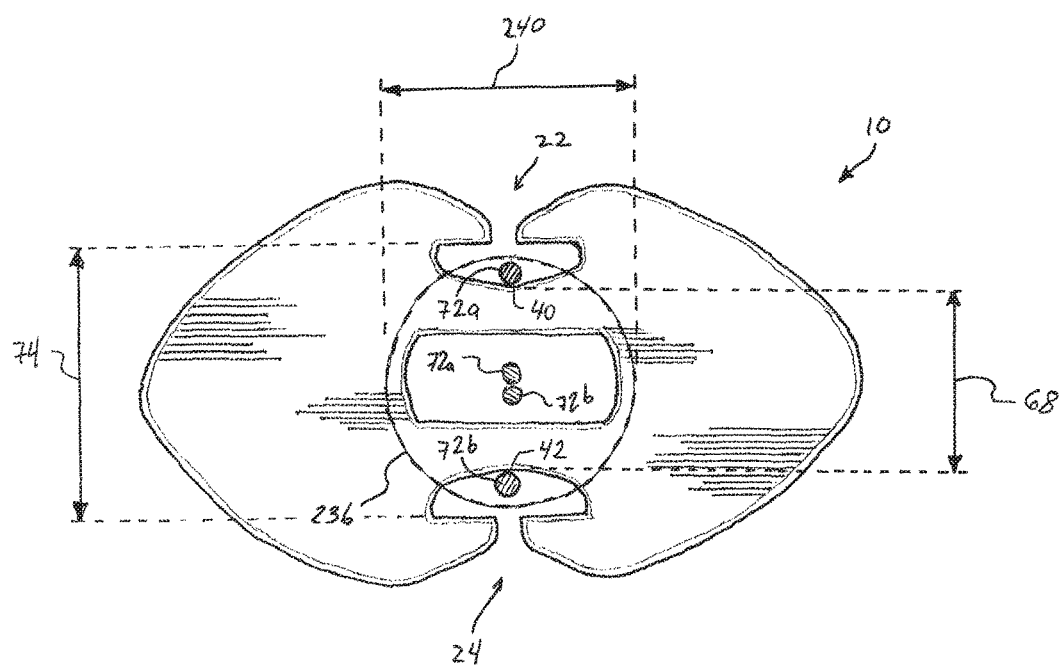
FIG. 10 illustrates a top view of an embodiment of a suture button showing the outline of a transosseous tunnel opening in accordance with the present disclosure.

Referring further to FIG. 1, second side notch 24 is open at its innermost point to an interior second suture dock 28 defined in body 12 of suture button 10. Second suture dock 28 includes a length in the longitudinal direction greater than its notch gap and its lateral width, providing a space for one or more sutures to be received. Second suture dock 28 includes a second suture dock interior wall having a "U" or "V" shape with a central indentation forming second suture dock seat 42. The sloping profile of the interior wall of second suture dock 28 allows a suture residing in second suture dock 28 to be centrally seated at the second suture dock seat 42 when tensioned, as seen in FIG. 10. As noted above with regard to first suture dock 26, the central alignment of a suture in second suture dock 28 at second suture dock seat 42 provides improved positioning of the suture for entry into a transosseous drill tunnel opening when suture button 10 is installed against a patient's bone.

In some embodiments, first notch 22 and first suture dock 26 are symmetric about the major longitudinal axis of body 12 with second notch 24 and second suture dock 28. This symmetry provides an identical side notch and suture dock on each side of suture button 10 and allows the device to readily accept one or more suture end loops around either end of suture button 10. This symmetry also allows each loop side to be received in its corresponding notch and to be centrally seated in its corresponding suture dock seat in a similar orientation.

Figure 7:
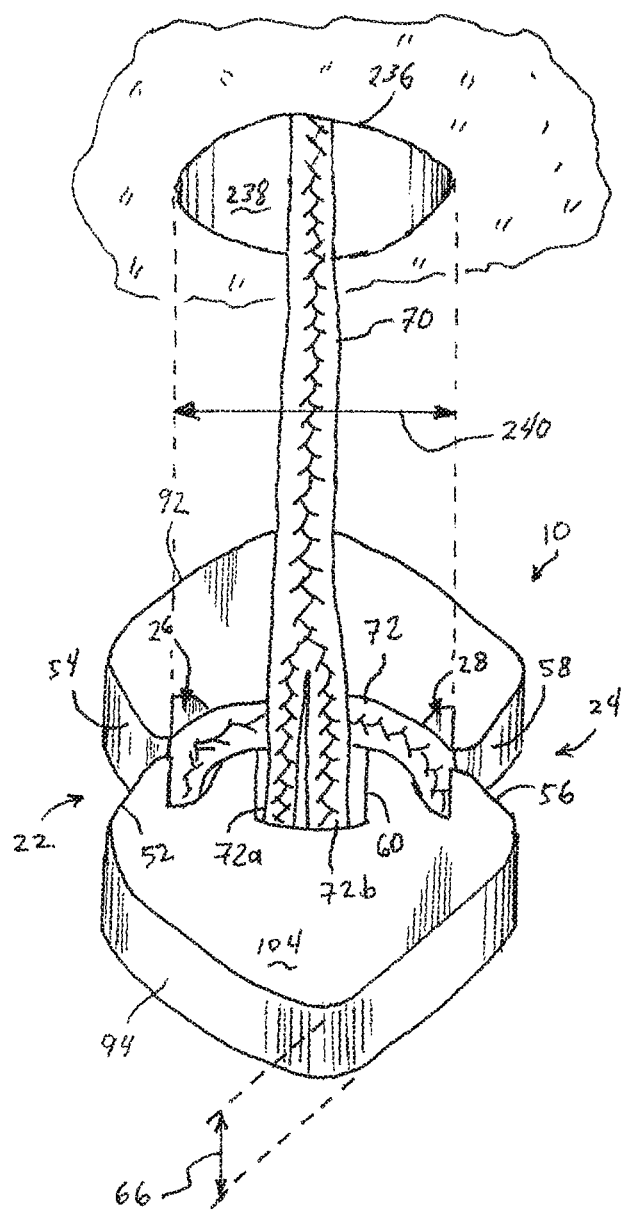
FIG. 7 illustrates a perspective view of an embodiment of a suture button having a suture installed thereon in accordance with the present disclosure.

Referring further to FIG. 1, another feature of suture button 10 includes a center passage 60 defined in body 12 between the anterior side 102 and the opposing posterior side 104, seen in FIG. 7. Center passage 60 is defined entirely through suture button 10 to provide a space for passage of one or more suture strands through suture button 10. As seen in FIG. 1, center passage 60 is positioned at a midpoint laterally between first and second notches 22, 24. Additionally, center passage 60 is positioned at a midpoint between first and second longitudinal ends 14, 16. Center passage 60 includes straight side walls and slightly curved concave end walls in some embodiments, as seen in FIG. 1.

Figure 2:
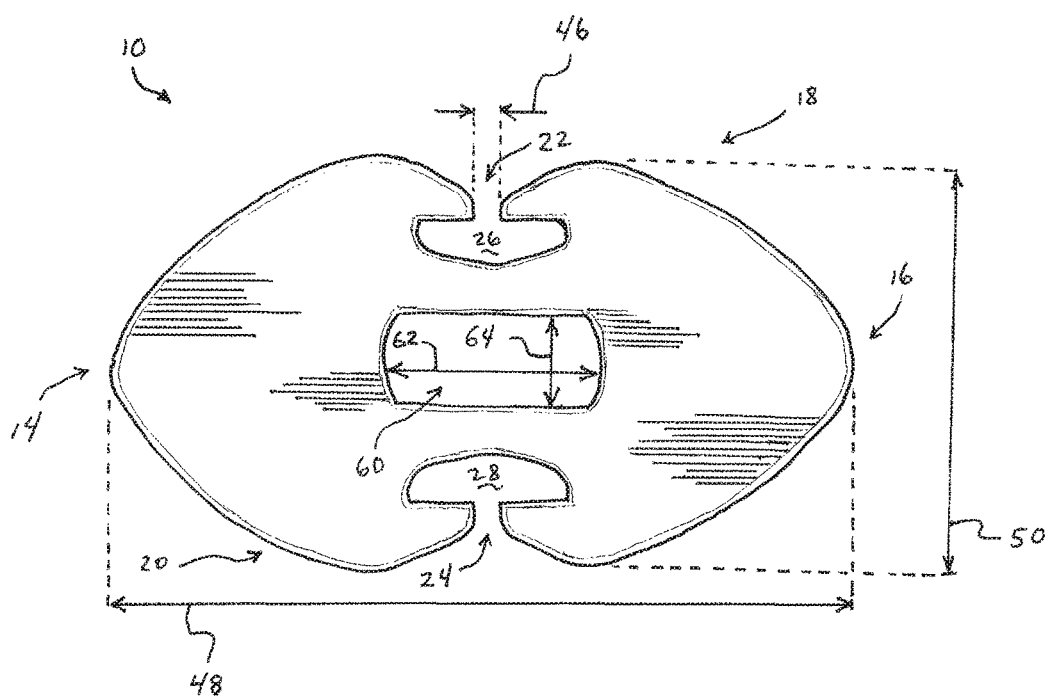
FIG. 2 illustrates a top view of an embodiment of a suture button in accordance with the present disclosure.

Center passage includes a center passage length 62 and a center passage width 64, shown in FIG. 2. In some embodiments, center passage length 62 is greater than center passage width 64. Center passage length 62 in some embodiments is between about six millimeters and about one millimeter. In further embodiments, center passage length 62 is between about 2.5 millimeters and about 4.5 millimeters. In additional embodiments, center passage length 62 is about 3.5 millimeters. Center passage width 64 in some embodiments is between about 0.5 millimeters and about three millimeters. In further embodiments, center passage width 64 is between about one millimeter and about two millimeters. In additional embodiments, center passage width 64 is about 1.6 millimeters. Center passage 60 includes a center passage length 62 slightly longer than the longitudinal length of first and second suture docks 62, 64. During use, one, two, three, four or more suture strands may pass through center passage 60 from either surface of suture button 10 to the other.

Figure 11:
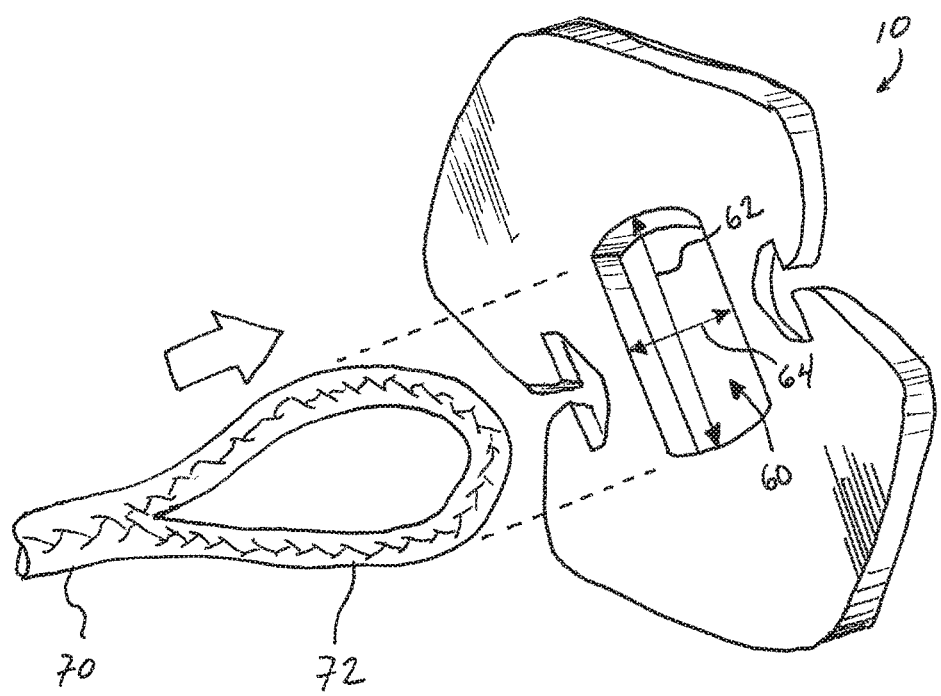
FIG. 11 illustrates a perspective view of an embodiment of a suture button and a suture with a fixed loop positioned for installation on the suture button in accordance with the present disclosure.

Center passage 60 in some embodiments includes an aspect ratio of center passage length divided by center passage width greater than 1.0, forming a center passage having an elongated shape. The elongated shape of center passage 60 provides a slit-shaped opening in some embodiments allowing for easier passage of a fixed loop 72 on a suture end as seen in FIG. 11. During some procedures, it is desirable to install a suture 70 having a fixed loop 72 onto suture button 10 by passing the fixed loop through center passage 60 and then looping the loop portion passed through the center passage back around the body 12, forming a lateral girth hitch with loop 72 positioned around suture button 10 as seen in FIG. 7. To initiate the installation of the fixed loop 72 onto suture button 10, the loop must be first inserted into center passage 60. A fixed loop 72 naturally has a flattened profile having a width much greater than its thickness. Using a conventional center passage having a uniform circular hole makes it difficult to insert the unique shape of the fixed loop through the body of the suture button 10. The present disclosure addresses this difficulty by providing a suture button 10 having a center passage 60 including a center passage aspect ratio of center passage length 62 divided by center passage width 64 between about one and about ten. In some embodiments, the center passage aspect ratio is between about one and about three. In additional embodiments, the center passage aspect ratio is between about two and about 2.4. By providing a center passage aspect ratio greater than about one in some embodiments, a fixed loop 72, as shown in FIG. 11, may be more easily inserted through center passage 60 on suture button 10.

Referring further to FIG. 2, suture button 10 includes a suture button length 48 and a suture button width 50. Suture button length 48 is defined as the longitudinal distance between first end 14 and second end 16. Suture button length 48 includes any suitable length to provide an anchor for retaining one or more suture strands during and/or after a surgical procedure. In some embodiments, suture button length 48 is between about five and about twenty millimeters. In further embodiments, suture button length 48 is between about ten and about fifteen millimeters. In additional embodiments, suture button length is about twelve millimeters. Similarly, suture button width 50 is defined as the distance between the lateral distance between the widest points on suture button 10. In some embodiments, suture button width 50 is defined between the outermost point on first side 18 and the outermost point on second side 20. Suture button width 50 includes any distance suitable for providing an anchor to retain one or more suture button strands during and/or after a surgical procedure. Suture button width 50 in some embodiments is between about three millimeters and about twenty millimeters. In further embodiments, suture button width 50 is between about five millimeters and about ten millimeters. In additional embodiments, suture button width 50 is about seven millimeters.

Referring further to FIG. 2, first notch 22 provides a passage for one or more suture strands into first suture dock 26. First notch 22 tapers down to form a central gap having a notch gap spacing 46. Notch gap spacing 46 includes the minimum gap spacing between the opposing projections protruding from body 12 to form the narrowest point in first notch 22 at the passage into first suture dock 26. Notch gap spacing 46 is dimensioned in some embodiments to correspond to a mean diameter of a suture strand to be used in a surgical procedure.

Figure 3:
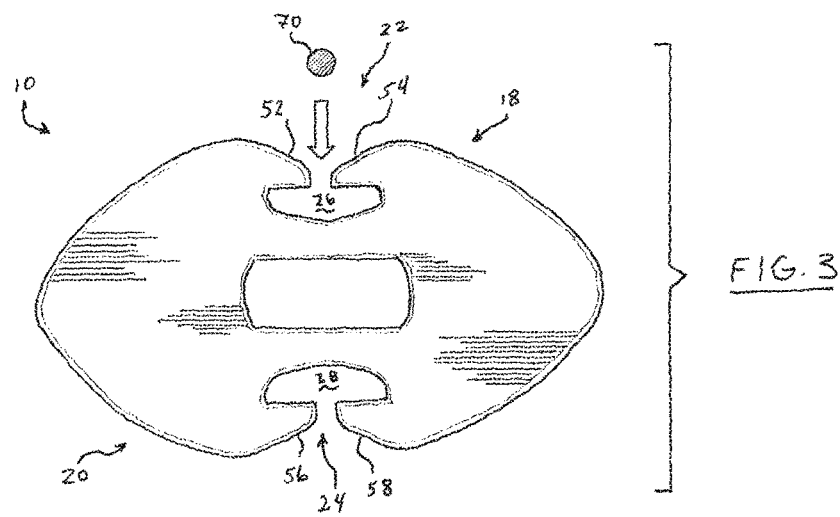
FIG. 3 illustrates a top view of an embodiment of a suture button in accordance with the present disclosure.
Figure 4:
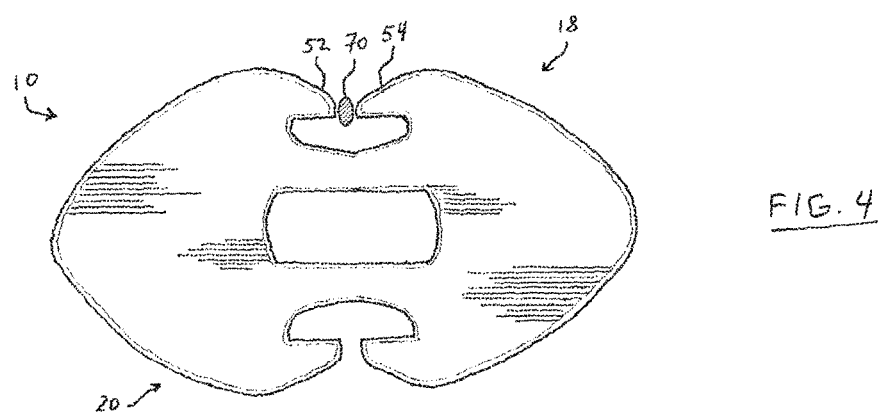
FIG. 4 illustrates a top view of an embodiment of a suture button in accordance with the present disclosure.
Figure 5:
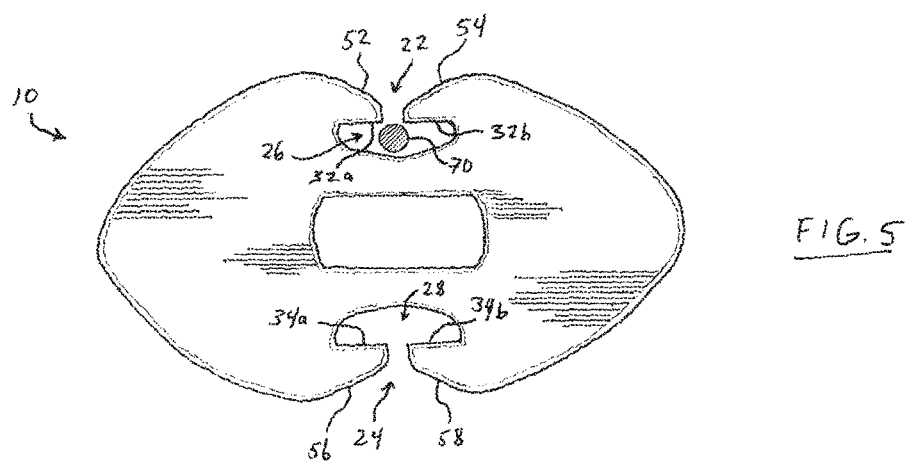
FIG. 5 illustrates a top view of an embodiment of a suture button in accordance with the present disclosure.

For example, as shown in FIGS. 3-5, a suture 70 may be positioned for insertion into the first suture dock 26 on suture button 10. Suture 70 may include a free strand of a suture material or may include a side portion of a loop of suture material. Suture 70 is initially received into first side notch 22. First side notch 22 includes a first ramp 52 and a second ramp 54. First and second ramps 52, 54 form a concave, tapered profile of body 12 along the region of first notch 22. The first and second ramps slope inwardly toward each other in a "V" shape, funneling the suture 70 toward the notch gap, as shown in FIG. 3 and FIG. 4. Notch gap spacing 46 is dimensioned to be slightly narrower than the mean diameter of the suture 70, thereby causing suture 70 to become slightly radially compressed, as seen in FIG. 4, as suture 70 passes from first side notch 22 into first suture dock 26. When suture 70 exits the narrow gap, the suture may expand radially back to its uncompressed diameter as it resides in the first suture dock 26. As further tension is applied to the suture 70, the additional slope of the interior wall of first suture dock 26 causes the suture 70 to become seated along the center of the first suture dock 26 at the first suture dock seat 40.

Similarly, second notch 24 includes third and fourth ramps 56, 58. Third and fourth ramps 56, 58 form a concave, tapered profile of body 12 along the region of second notch 24. The third and fourth ramps slope inwardly toward each other in a "V" shape, funneling any suture entering second notch 26 toward the notch gap. Second notch 24 includes a similar notch gap spacing 46 dimensioned to be slightly more narrow than the mean diameter of a suture to be used, thereby causing the suture to become slightly radially compressed when the suture passes from second notch 24 to second suture dock 28. When the suture exits the narrow gap, the suture may expand radially back to its uncompressed diameter as it resides in the second suture dock 28. As further tension is applied to the suture while it resides in second suture dock 28, the additional slope of the interior wall of second suture dock 28 causes the suture to become seated along the centerline of the second suture dock 28 at the second suture dock seat 42.

In some embodiments, notch gap spacing 46 on both first notch 22 and second notch 24 is configured to be slightly smaller than the mean diameter of a desired suture material, including either monofilament suture material or braided suture material. For example, notch gap spacing 46 in some embodiments is about 0.25 millimeters, and is configured for use with a suture material having a mean diameter greater than about 0.25 millimeters such that the suture must be slightly radially compressed to pass from first or second notch 22, 24 into first or second suture dock 26, 28, respectively.

As shown in FIG. 5, first notch 22 and second notch 24 each include a substantially flat outer suture dock wall, forming right angles at the openings from each respective suture dock 26, 28 outwardly away from the suture body. Because each outer suture dock wall is substantially flat in some embodiments, and because the notch gap spacing 46 is slightly less than the mean diameter of a suture being used, each suture is retained within its corresponding suture dock and is prevented from being able to inadvertently back out of the suture dock through the notch gap. This design further helps retain each suture segment in its corresponding suture dock after initial entry into the suture dock.

Figure 6:
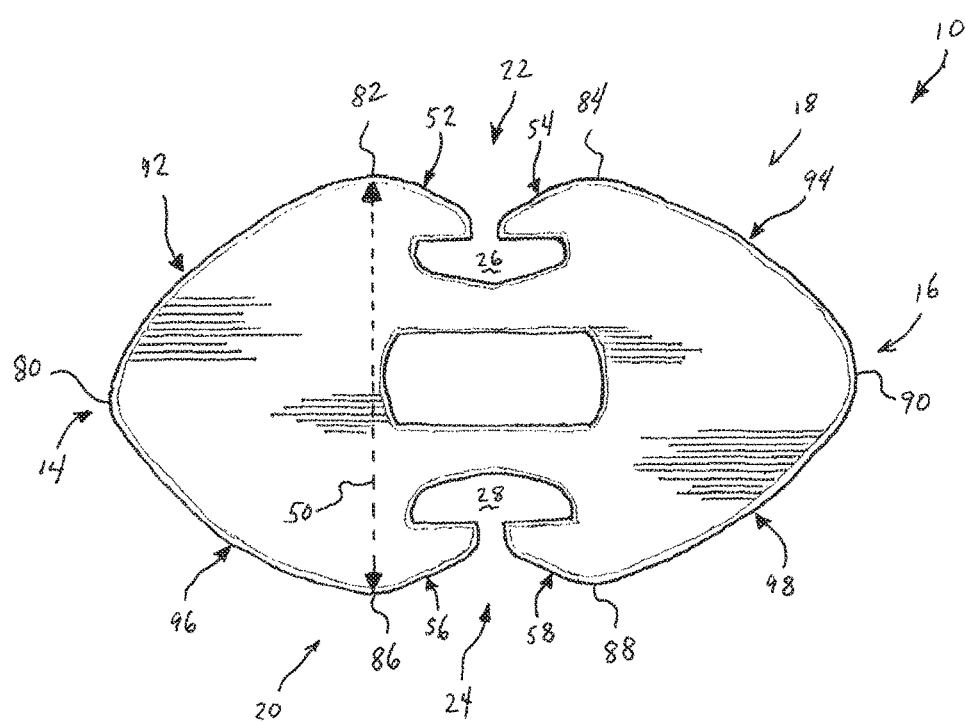
FIG. 6 illustrates a top view of an embodiment of a suture button in accordance with the present disclosure.

In some embodiments, suture button 10 is configured to be attached to a suture 70 including a fixed loop 72 at its end, as shown in FIGS. 7, 8, 9 and 11. More specifically, a fixed loop 72 may be passed through center passage 60 and then slid over either first end 14 or second end 16 to form a girth hitch around the body 12 of suture button 10. As noted above, one feature allowing use with a fixed loop is the center passage 60 having an aspect ratio greater than 1.0 to allow easier insertion of the fixed loop. Additional other features provide improved ease of use with a fixed loop girth hitch attachment. For example, as shown in FIG. 6, first end 14 has a tapered shape sloping toward first end point 80, and second end 16 has a tapered shape sloping toward second end point 90. Additionally, first side 18 includes a first ramp 92 sloping toward first end point 80 and a second ramp 94 sloping toward second end point 90. Similarly, second side 20 includes a third ramp 96 sloping toward first end point 80 opposing first ramp 92, and second side 20 also includes a fourth ramp 98 sloping toward second end point 90 opposing second ramp 94. Thus, each longitudinal end of suture button 10 includes a generally tapered shape to ease positioning of the loop portion back onto either longitudinal end after the loop has passed through center passage 60.

As shown further in FIG. 6, first side 18 includes a first lateral apex 82 and a second lateral apex 84. Second side 20 includes a third lateral apex 86 and a fourth lateral apex 88. First lateral apex 82 is opposite third lateral apex 86 forming a first lateral apex pair on the left side of the suture button 10, and second lateral apex 84 is opposite fourth lateral apex 88 forming a second lateral apex pair on the right side of the suture button 10. First and second lateral apex pairs each form the widest points on suture button 10 in some embodiments, as seen in FIG. 6. For example, the first lateral apex pair defines the outermost lateral dimension on suture button 10, and is equal to body width 50 in some embodiments. The second lateral apex pair similarly defines the same lateral dimension as the first lateral apex pair in some embodiments. In other embodiments, first and second lateral apex pairs may form different dimensions to accommodate different loop sizes on each longitudinal end of suture button 10.

The lateral sides of suture button 10 between neighboring apex pairs on the same side begins to slope back inwardly toward the center of body 12. For example, between first lateral apex 82 and second lateral apex 84, first ramp 52 slopes inwardly toward first suture dock 26 as seen in FIG. 6. Similarly, between first lateral apex 82 and second lateral apex 84, second ramp 54 slopes inwardly toward first suture dock 26. On the opposite side of suture button 10, between third lateral apex 86 and fourth lateral apex 88, third ramp 56 and fourth ramp 58 both slope inwardly toward second suture dock 26. Thus, when a fixed loop 72 is slid through center passage 60 and back onto either first longitudinal end 14 or second longitudinal end 16, the loop will first slide over either first or second lateral apex pair, respectively, and then slide along first and third ramps 52, 56 or second and fourth ramps 54, 58 toward a suture dock.

Figure 9:
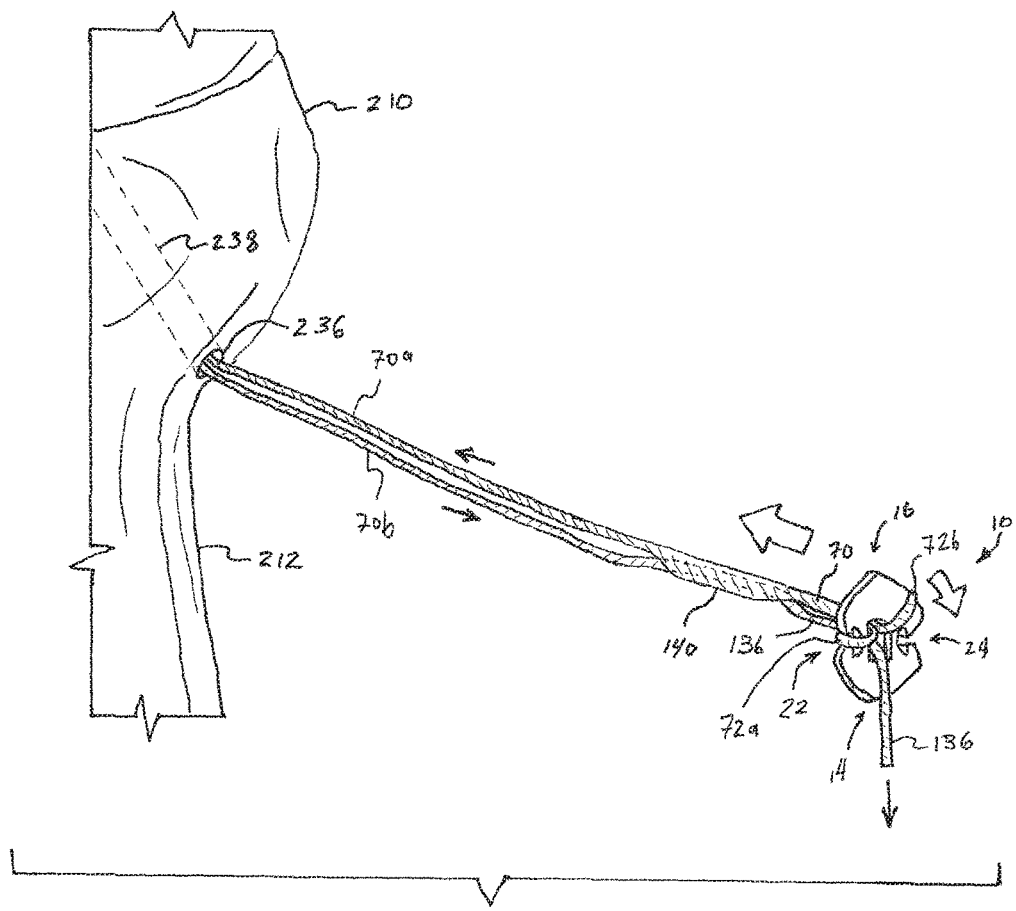
FIG. 9 illustrates a top view of an embodiment of a suture button in accordance with the present disclosure.

Referring to FIG. 9, an example of a fixed loop being slid into place in a girth hitch configuration on suture button 10 is shown. A first loop side 72a slides into first notch 22, and a second loop side 72b slides into second notch 24. In the example shown in FIG. 9, the fixed loop 72 is being slid over the second longitudinal end 16 after being inserted through the center passage. Alternatively, the fixed loop could be slid over the first longitudinal end 14 after being inserted through the center passage.

Figure 8:
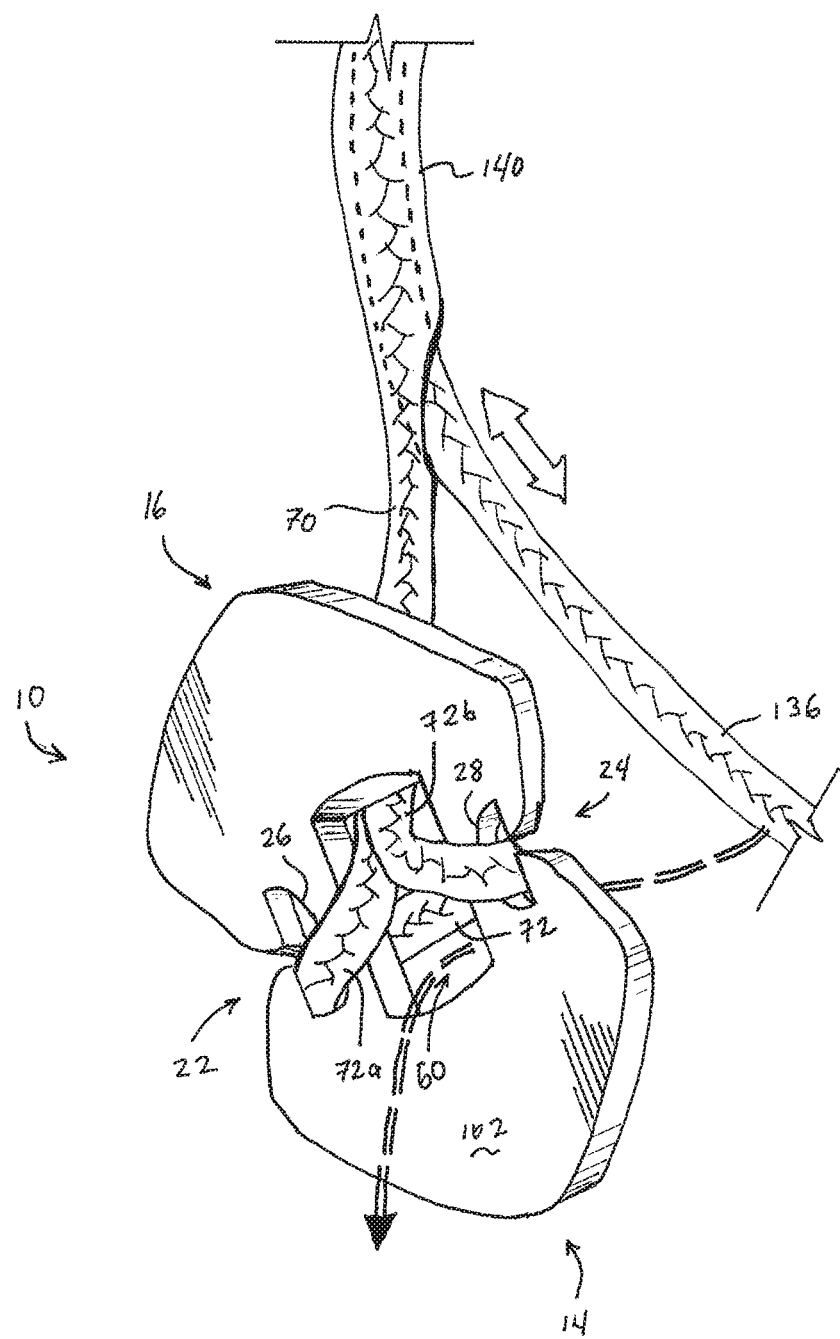
FIG. 8 illustrates a perspective view of an embodiment of a suture button in accordance with the present disclosure.

Another example of a fixed loop installed on a suture button 10 using a girth hitch attachment is shown in FIG. 7 and FIG. 8. As shown in FIG. 7, a suture 70 includes a loop 72 first inserted downwardly through center passage 60 from the posterior side 104 of suture button 10. The loop is then positioned back around a longitudinal end of the suture button 10 forming a girth hitch around the body of the suture button 10. In the embodiment shown in FIG. 7 and FIG. 8, the fixed loop was slid back over the first longitudinal end 14. A first loop side 72a is received in first suture dock 26, and a second loop side 72b is received in second suture dock 28. When tension is applied to the suture 70 the hitched loop around suture button 10 becomes tighter, drawing first loop side 72a and second loop side 72b in even more tightly against suture button 10. This causes first loop side 72a to be seated in the "U" shaped or "V" shaped first suture dock seat 40, and causes the second loop side 72b to be seated in the "U" shaped or "V" shaped second suture dock seat 42, shown in FIG. 10.

As shown in FIG. 7 and FIG. 8, during installation, first ramp 52 and second ramp 54 in first notch 22 cause first loop side 72a to be funneled toward the centerline of the suture button 10. First loop side 72a then becomes slightly radially compressed as it passes through the notch gap in first notch 22. First loop side 72a then snaps back to its original uncompressed size as it enters first suture dock 26. Similarly, third ramp 56 and fourth ramp 58 in second notch 24 cause second loop side 72b to be funneled toward the centerline of the suture button 10. Second loop side 72b then becomes slightly radially compressed as it passes through the notch gap in second notch 24. Second loop side 72b then snaps back to its original compressed size as it enters second suture dock 28.

As shown in FIG. 7, suture button 10 includes a body thickness 66 in some embodiments. Body thickness 66 is the distance between anterior side 102, shown in FIG. 8, and posterior side 104, shown in FIG. 7. Posterior side 104 is generally defined as the side of suture button 10 that faces the bone and is placed adjacent the drill tunnel opening. Anterior side 102 is generally defined as the side of suture button 10 that faces away from the drill tunnel opening when installed. In some embodiments, body thickness 66 is between about 0.5 millimeters and about four millimeters. In further embodiments, body thickness 66 is between about one millimeter and about two millimeters. In additional embodiments, body thickness 66 is about 1.5 millimeters. Body thickness 66 may include any suitable material thickness to provide stability and rigidity for tensioning a suture. In some embodiments, suture body 10 includes a uniform body thickness. In further embodiments, suture body 10 includes a non-uniform body thickness across body 12. In some applications, it is desirable to provide a body thickness 66 that allows suture button 10 to deflect slightly along its major longitudinal axis toward the drill tunnel opening to further maintain tension and to keep the button at a desired location against the bone.

Suture button 10 may be used in numerous types of procedures. In some embodiments, suture button 10 is used with a knotless suture construct as shown for example in FIG. 8 and FIG. 9. The knotless suture construct includes a suture 70 having a fixed loop 72 at one end. The fixed loop 72 is affixed around the body of the suture button 10 in a girth hitch, as previously described. Suture 70 exits the central passage 60 on suture button 10 and extends toward tissue to be engaged. For example, as shown in FIG. 9, suture 70 extends from button 10 toward a knee 210. Suture 70a enters a lower opening 236 of a transosseous drill tunnel 238 through the patient's tibia 212 and knee 210. Suture 70 extends through drill tunnel 238 to the site of a meniscal root tear in this embodiment. The suture 70b passes through the tissue or another joining structure at the root tear site and then exits the lower opening 236. A knotless suture construct includes a self-cinching sleeve 140 in some embodiments. Sleeve 140 is formed in suture 70 near fixed loop 72 between suture button 10 and lower opening 236. Free suture end 136 extending back toward suture button 10 from suture 70b passes freely through sleeve 140. Free suture end 136, shown in FIG. 8 after passing through sleeve 140, may then be inserted through center passage 60, as shown in FIG. 9. The free suture end 136 is then pulled relative to suture button 10, causing the suture button 10 to be drawn closer to lower opening 236 as suture 70 slides through the tissue or joining structure at the repair site. Once the free suture end 136 is drawn tight, suture button is pulled directly against the bone in knee 210, and sleeve 140 is cinched tightly against suture 70b causing a gripping effect that prevents the applied tension from being released. Fixed loop 72 formed in a girth hitch around suture button 72 forms a rigid anchor against which tension may be pulled. Suture button 10 will then maintain its position, held in place against the bone using the tension applied by suture 70. The tag portion of free suture end 136 may then be trimmed after a desired tension is applied.

When suture button 10 is pulled against the bone such that suture button 10 is adjacent lower opening 236 on tunnel 238, it is generally desirable that the suture material not be impinged upon the edge of lower opening 236. Such impingement may prevent a surgeon from being able to pull a desirable tension on the suture 70. Additionally, such impingement may cause inadvertent wear or stress on the suture, leading to a weakening or failure of the suture material.

Another aspect of the present disclosure provides a suture button for surgical procedures configured to provide axial alignment of the suture 70 exiting center passage 60 with the axial bore of tunnel 238. Because the hitched portion of suture 70 extending toward tunnel 238 includes the section extending from center passage 60, the suture 70 entering lower opening 236 extends from suture button 10 at a position very near the lateral and longitudinal center of suture button 10, as shown in FIG. 7. Thus, when suture button 10 is positioned adjacent the bone structure at the lower opening 236 after suture 70 is pulled tight, the portion of suture 70 exiting center opening 60 and entering tunnel 238 is axially aligned near the center of tunnel 238, and suture button 10 is centered over lower opening 236.

Additionally, in some embodiments, suture button 10 is dimensioned such that first loop side 72a housed in first side dock 26 and second loop side 72b housed in second side dock 28 when fully seated are laterally spaced such that neither contacts the bone wall adjacent lower opening 236. For example, as seen in FIG. 10, suture button 10 is dimensioned such that a bridge width 68 is defined as the narrowest distance between first dock seat 40 and second dock seat 42. The bridge width 68 plus two times the suture mean diameter is less than tunnel diameter 240. As such, when a fixed loop is installed around suture button 10 such that a first loop side 72a is retained in first dock seat 40 and a second loop side 72b is retained in second dock seat 42, the outer lateral distance between first loop side 72a and second loop side 72b is less than tunnel diameter 240. This configuration allows the suture button 10 to be installed such that no portion of the suture material is impinged by the bone tissue adjacent lower opening 236. This configuration allows a stronger attachment between suture button 10 and the bone structure adjacent lower opening 236 without any intermediate suture material being pinched between suture button 10 and the bone surface. In some embodiments, to ensure clearance between the suture material and the lower opening 236, suture body includes a notch distance 74 defined as the distance between the outer wall on first side dock 26 and the outer wall on second side dock 28. Notch distance 74 is equal to drill tunnel diameter in some embodiments to provide adequate clearance. In additional embodiments, the ratio of tunnel diameter 240 to notch distance 74 is between about 0.9 and about 2.0 to provide adequate clearance. In further embodiments, the ratio of tunnel diameter 240 to notch distance 74 is about 1.0 to provide adequate clearance. In further embodiments, the ratio of tunnel diameter 240 to bridge width 68 is between about 1.0 and about 2.0 to provide adequate clearance.

Figure 12:
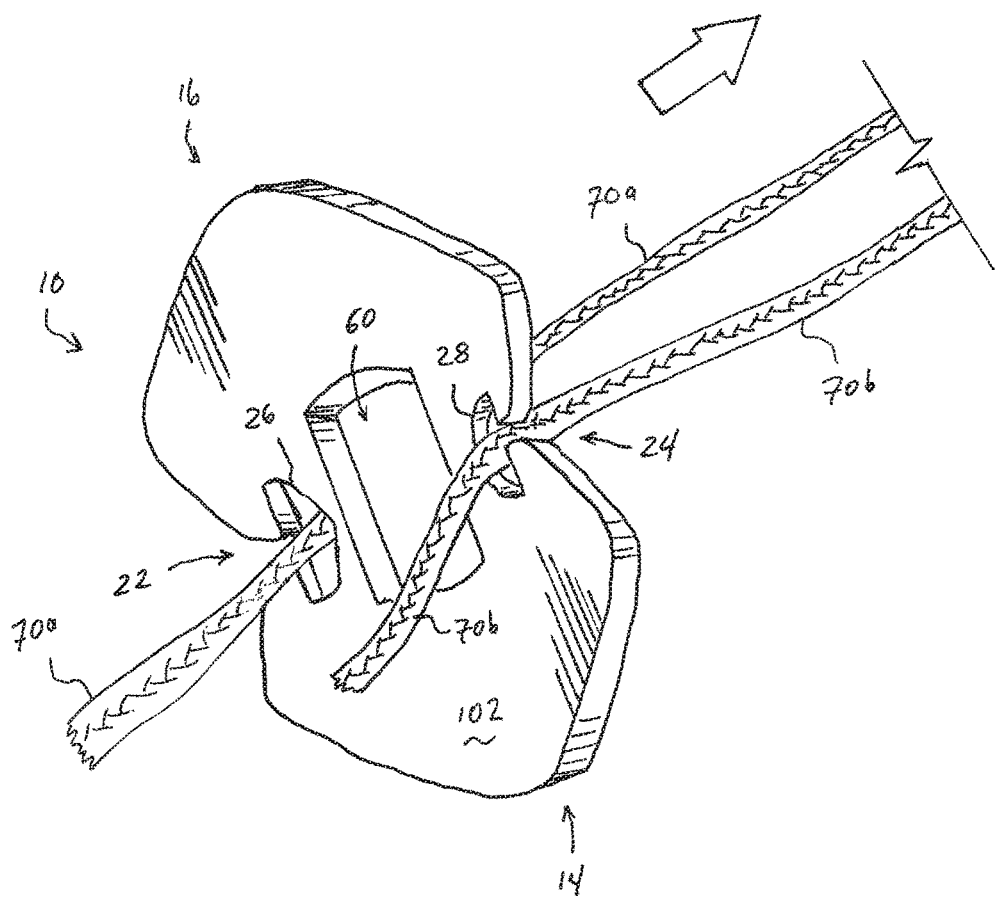
FIG. 12 illustrates a perspective view of an embodiment of a suture button and a suture with a conventional knotted suture.
Figure 13:
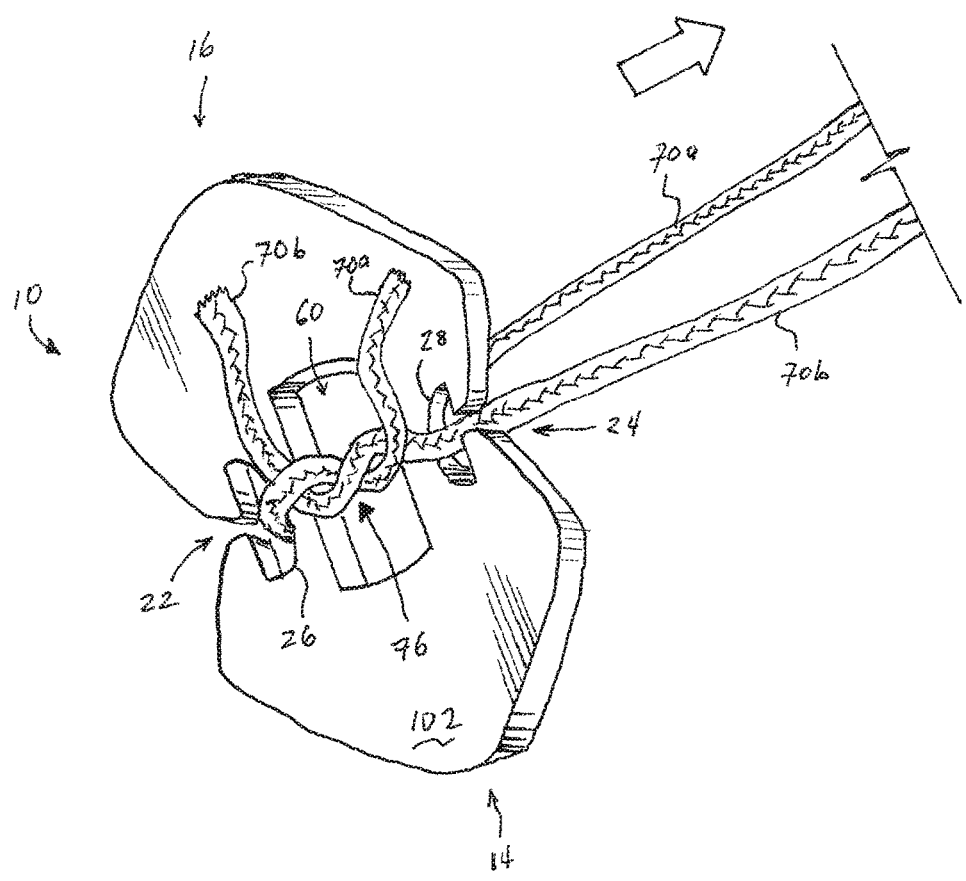
FIG. 13 illustrates a perspective view of an embodiment of a suture button and a suture using a conventional suture knot to tighten the suture construct in accordance with the present disclosure.
Figure 14:
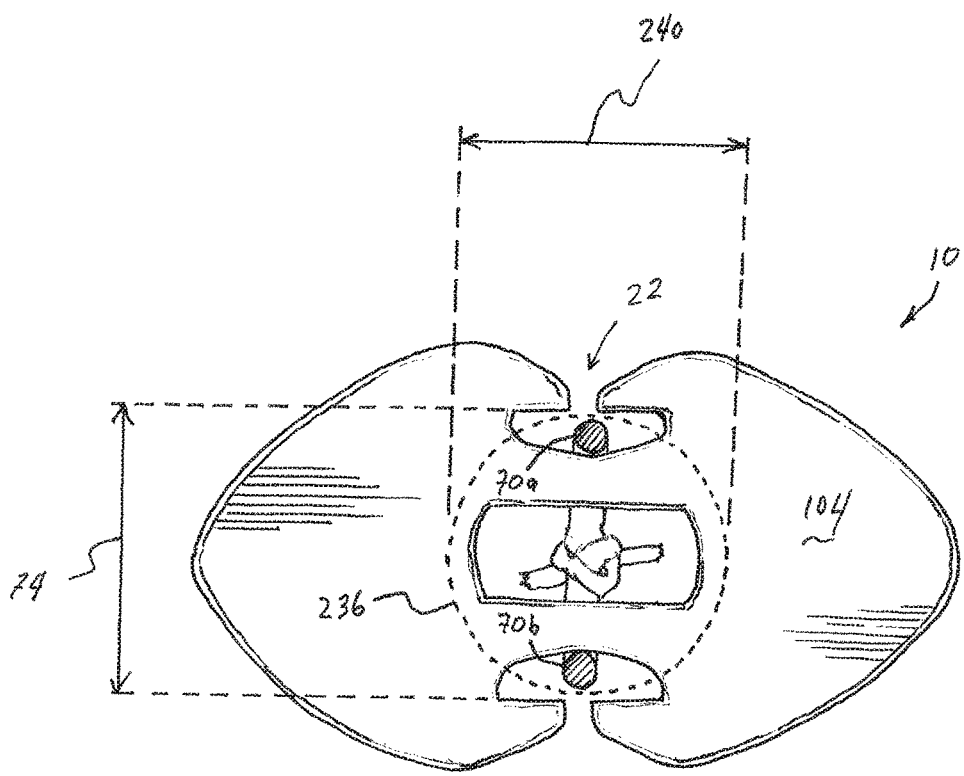
FIG. 14 illustrates a top view of an embodiment of a suture button showing the outline of a transosseous tunnel opening in accordance with the present disclosure

Referring further to the drawings, FIGS. 12-14 illustrate an embodiment of a suture button 10 of the present disclosure positioned for use with a conventional knotted suture construct. When used with conventional knotted suture constructs and knotted suture tightening techniques, suture button 10 provides advantages over traditional suture buttons known in the art for several reasons. These advantages include suture self-centering and "locking" in place in first and second suture docks 26, 28 via first and second notches 22, 24, and also axial suture alignment with the drill tunnel when tightened to prevent impingement of the suture against the bone at the drill tunnel opening.

For example first and second notches 22, 24 allow suture material to slide into first and second docks 26, 28, and also prevent sutures from inadvertently backing out of first and second suture docks 26, 28, respectively during tightening. For example, first and second sutures 70a, 70b extend from a transosseous drill tunnel opening toward suture button 10. First suture 70a includes a first free tag end slid laterally through first notch 22 into first suture dock 26. First suture 70a is held in first suture dock 26 and is prevented from easily backing out through first notch 22 by first and second ramps 52, 54. Similarly, second suture 70b includes a second free tag end slid laterally through second notch 24 into second suture dock 28. Second suture 70b is held in second suture dock 28 and is prevented from easily backing out through second notch 24 by third and fourth ramps 56, 58.

As shown in FIG. 12, suture button 10 is positioned with its posterior side 104 facing toward the distal transosseous drill tunnel opening and with its anterior side 102 facing away from the opening. A surgeon may hold the free tag ends of first and second sutures 70a, 70b and freely slide suture button 10 toward the distal transosseous opening 236 until the posterior side 104 of suture button 10 is in contact with the bone tissue.

Once suture button 10 in place, or while suture button 10 is being advanced toward the desired location against the bone, the surgeon forms one or more knots on the anterior side 102 of suture button 10 using the first and second free tag ends of first and second sutures 70a, 70b. For example, as shown in FIG. 13, a single-wrap throw may be formed between first and second sutures 70a, 70b on anterior side 102 of suture button 10. Each tag end may be pulled tight to further advance suture button 10 toward the bone. Alternatively, a double-wrap first throw may be formed on anterior side 102 of suture button 10. Once a suitable first knot 76 such as a tight single-wrap or double-wrap first throw is established, numerous types of suture knots may be formed on anterior side 102 of suture button 10 to provide a desired connection between the first and second free tag ends of first and second sutures 70a, 70b. Such knots may include but are not limited to a square knot, a granny knot, a surgeon's knot, a slip knot, or any other suitable suture knot or combination of suture knots to secure first and second sutures 70a, 70b together on anterior side 102 of suture button 10.

Another aspect of suture button 10 providing an advantage over conventional suture buttons in some embodiments relates to suture alignment with distal transosseous drill tunnel opening 236. As shown in FIG. 14, suture button 10 is dimensioned such that first and second sutures 70a, 70b are laterally aligned with distal transosseous drill tunnel opening 236 in some embodiments such that neither first suture 70a nor second suture 70b rubs against the drill tunnel opening surface when each suture is fully seated in its corresponding suture dock. This configuration also provides a self-centering of suture button 10 relative to the drill tunnel opening as the suture is tightened. In some such embodiments, notch distance 74 is less than drill tunnel opening diameter 240, providing lateral clearance for first and second sutures 70a, 70b as they pass from the suture button 10 into the drill tunnel. This configuration provides an advantage over many conventional suture buttons that fail to include a geometry allowing axial alignment and lateral clearance of first and second sutures 70a, 70b as they pass into the drill tunnel opening, thereby causing the suture button to undesirably impinge on the suture material adjacent the drill tunnel opening.

Thus, although there have been described particular embodiments of the present invention of a new and useful Suture Button for Surgical Procedure, it is not intended that such references be construed as limitations upon the scope of this invention except as set forth in the following claims.

What is claimed is:

1. A suture button apparatus, comprising:
    a body having a major longitudinal axis and a first longitudinal end, a second longitudinal end, a first lateral side, a second lateral side, an anterior surface, and a posterior surface;
    a first suture dock defined in the first lateral side;
    a second suture dock defined in the second lateral side;
    a center passage defined through the body from the anterior surface to the posterior surface, the center passage positioned at a midpoint laterally between the first and second suture docks, wherein the center passage is also positioned at a midpoint between first and second longitudinal ends;
    a first tapered notch defined in the first lateral side open to the first suture dock, the first tapered notch including a substantially flat outer suture dock wall; and
    a second tapered notch defined in the second lateral side open to the second suture dock,
    wherein the first tapered notch and first suture dock are symmetric about the major longitudinal axis of the body with the second tapered notch and the second suture dock, respectively.

2. The apparatus of claim 1, wherein the first longitudinal end is tapered toward a first longitudinal point.

3. The apparatus of claim 2, wherein the second longitudinal end is tapered toward a second longitudinal point opposite the first longitudinal point.

4. The apparatus of claim 1, wherein the body has a longitudinal length and a lateral width, and
    wherein the longitudinal length is greater than the lateral width.

5. The apparatus of claim 1, wherein the first side notch defines a first notch gap having a first notch gap spacing.

6. The apparatus of claim 5, wherein the first suture dock includes a longitudinal dock length in a longitudinal direction and a lateral dock width in a lateral direction, and
    wherein the longitudinal dock length is greater than lateral dock width and greater than the first notch gap spacing.

7. The apparatus of claim 6, wherein the center passage includes a center passage length and a center passage width, and
    wherein the center passage length is greater than the center passage width.

8. The apparatus of claim 7, wherein the center passage length is greater than the longitudinal dock length.

9. The apparatus of claim 1, wherein the first lateral side includes a first lateral apex and a second lateral apex, and
    wherein the second lateral side includes a third lateral apex and a fourth lateral apex.

10. The apparatus of claim 9, wherein the first lateral apex is opposite the third lateral apex forming a first apex pair, and wherein the second lateral apex is opposite the fourth lateral apex forming a second apex pair.

11. The apparatus of claim 10, wherein the first apex pair and the second apex pair define a widest lateral dimension of the body.

12. The apparatus of claim 11, wherein the first lateral side between the first lateral apex and the second lateral apex slope inwardly toward the first suture dock, and
wherein the second lateral side between the third lateral apex and the fourth lateral apex slope inwardly toward the second suture dock.

\* \* \* \* \*